(12) United States Patent
Perovitch et al.

(10) Patent No.: US 8,517,982 B2
(45) Date of Patent: Aug. 27, 2013

(54) DEVICE FOR PACKAGING AND DELIVERING ACTIVE PRINCIPLES IN A HYDROALCOHOLIC SOLUTION

(76) Inventors: Philippe Perovitch, Le Temple (FR); Marc Maury, Saint Medard En Jalles (FR)

( * ) Notice: Subject to any disclaimer, the term of this patent is extended or adjusted under 35 U.S.C. 154(b) by 99 days.

(21) Appl. No.: 13/133,054

(22) PCT Filed: Dec. 4, 2009

(86) PCT No.: PCT/FR2009/052413
§ 371 (c)(1), (2), (4) Date: Jun. 6, 2011

(87) PCT Pub. No.: WO2010/063978
PCT Pub. Date: Jun. 10, 2010

(65) Prior Publication Data
US 2011/0238008 A1    Sep. 29, 2011

(30) Foreign Application Priority Data

Dec. 5, 2008   (FR) ..................................... 08 58314

(51) Int. Cl.
*A61M 37/00*   (2006.01)
(52) U.S. Cl.
USPC ............................... 604/87; 604/88; 604/181
(58) Field of Classification Search
USPC ............. 604/87–88, 131–132, 138–139, 153, 604/216, 82, 181, 185, 187, 212; 222/633
See application file for complete search history.

(56) References Cited

U.S. PATENT DOCUMENTS

| 3,802,604 | A  | * | 4/1974  | Morane et al. ................. 222/83 |
| 5,827,235 | A  |   | 10/1998 | Beaver |
| 5,860,569 | A  |   | 1/1999  | Gregoire |
| 7,211,069 | B2 | * | 5/2007  | Lehmann ....................... 604/198 |
| 2007/0005027 | A1 |   | 1/2007  | Talamonti |
| 2007/0009490 | A1 | * | 1/2007  | Conte et al. ................. 424/93.4 |

FOREIGN PATENT DOCUMENTS

| EP | 0812775 A1 | 12/1997 |
| WO | 00/53507 A1 | 9/2000 |

OTHER PUBLICATIONS

International Preliminary Report on Patentability issued on Jun. 7, 2011 for counterpart application PCT/FR2009/052413.

* cited by examiner

*Primary Examiner* — Theodore Stigell
(74) *Attorney, Agent, or Firm* — Sughrue Mion, PLLC

(57) ABSTRACT

The invention provides a packaging and administering device for administering a hydro-alcoholic solution by passing through a mucous membrane, the device comprising a deformable container for receiving at least one first fraction of the solution, a base that is secured to the container, and an administering tube that is secured to the base and that is suitable for receiving at least one second fraction of the solution, and that includes a cap. The tube includes a chamber for containing the at least one second solution and that is defined by two membranes, and the cap is movable in translation between two extreme positions and includes a needle for coming to pierce the two membranes in one of the extreme positions.

9 Claims, 5 Drawing Sheets

Figure 1:
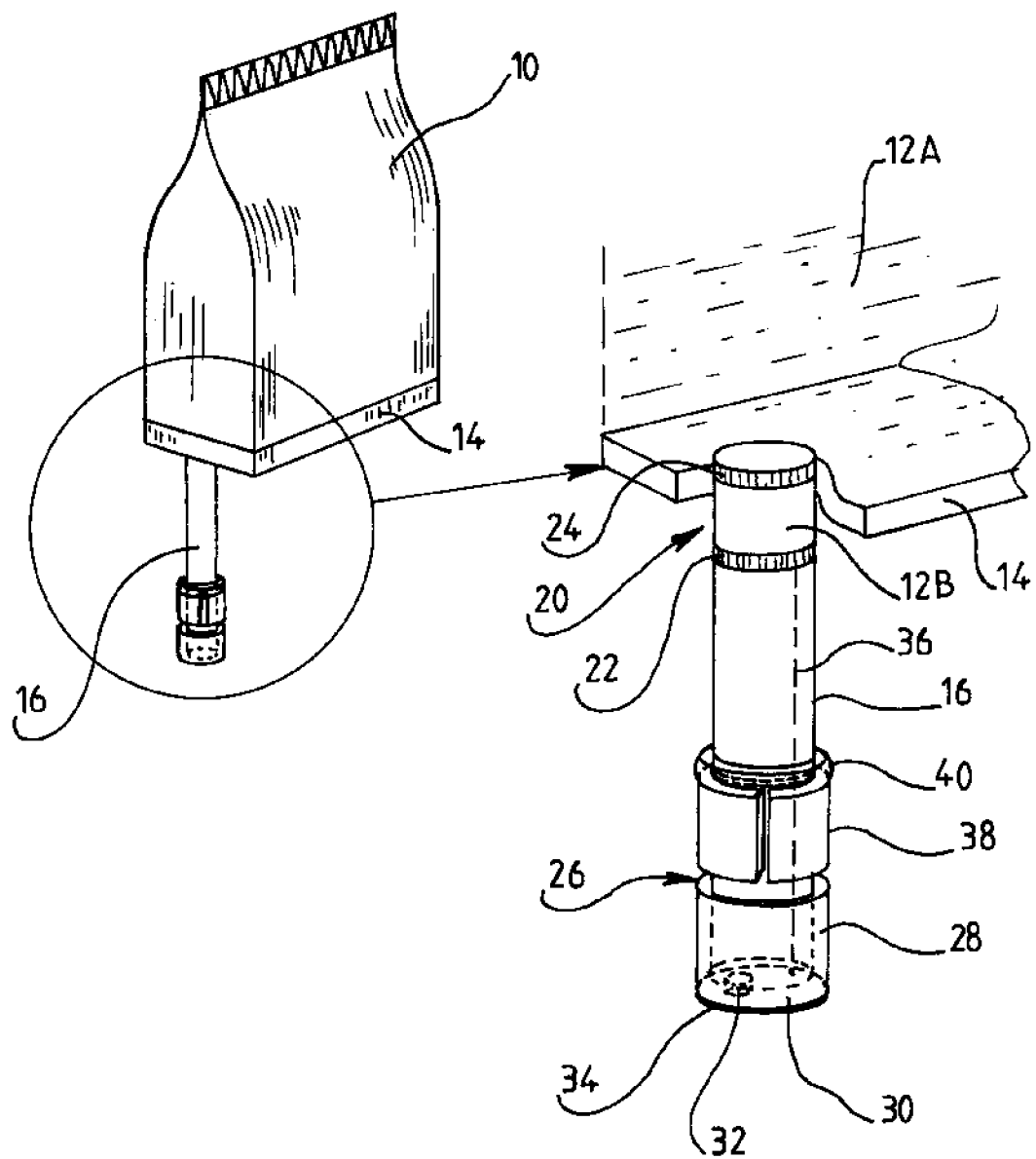

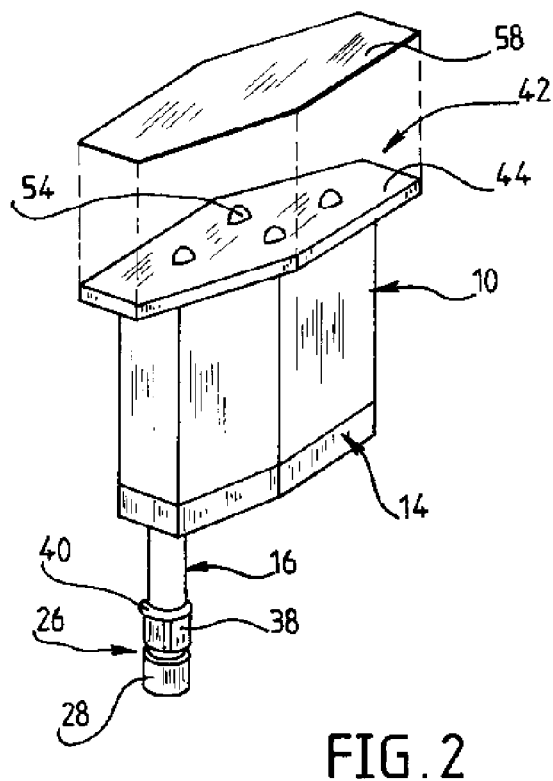
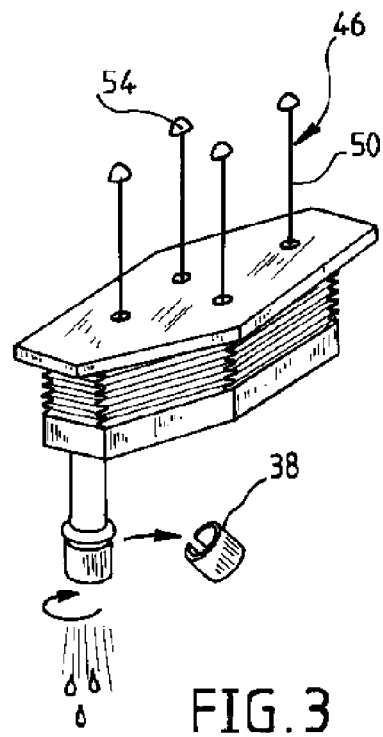
FIG.2　　　FIG.3
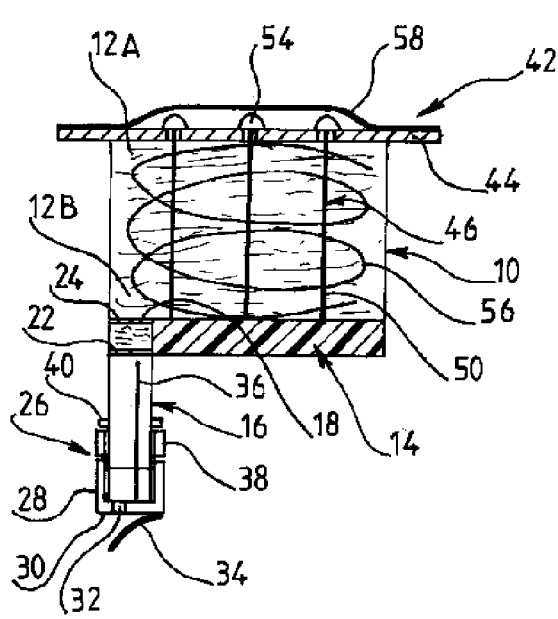
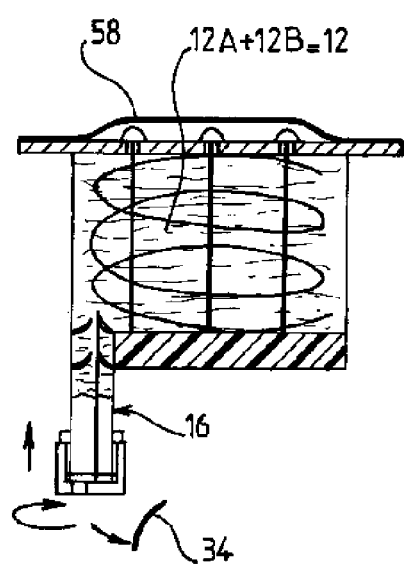
FIG.4　　　FIG.5

DEVICE FOR PACKAGING AND DELIVERING ACTIVE PRINCIPLES IN A HYDROALCOHOLIC SOLUTION

CROSS REFERENCE TO RELATED APPLICATIONS

This application is a National Stage of International Application No. PCT/FR2009/052413, filed Dec. 4, 2009, which claims priority from French Patent Application No. 0858314, filed Dec. 5, 2008, the contents of all of which are incorporated herein by reference in their entirety.

The present invention relates to a packaging and administering device for administering active principles in a hydro-alcoholic solution.

Increasingly, it is desired to administer drugs in liquid form, in particular in the form of solutions that are suitable for enabling active ingredients to be diffused through the mucous membranes covering the oral cavity by permeation under the tongue, via the cheeks, and/or via the gums.

This method of permucosal administration is very advantageous since it makes possible almost-instantaneous systemic pharmacological action and bioavailability as a result of the active principle(s) deposited in contact with the mucous membrane passing in a few seconds.

This rapid and targeted action that is obtained with small doses of active principle(s), thus avoids numerous side effects associated with metabolizing drugs (digestion, liver) before achieving systemic, organic, and tissular pharmacological availability of the drug.

However, the packaging of such formulations and their administration to patients pose a certain number of constraints.

In particular, it is generally necessary to provide single-dose packaging that is easy to use and safe, having a first safety parameter which is to avoid dangerous overdosing.

In addition, for hydro-alcoholic solutions for oral permucosal passage, it is essential to preserve the stability of the solution, to preserve the precise alcohol level of the formulation, and to protect the active principle(s) from being spoilt or degraded.

Various single-dose packaging devices are known, in particular small sterile bottles or sachets for drinkable forms for pouring into a glass after opening. Such containers do not make it possible to guarantee good administration, by oral permucosal passage, of a drug presented in hydro-alcoholic solution having a high degree of alcohol.

Also known, in the drug packaging industry in particular, is the flexible "stick" that is very attractive because of its cost and its speed of manufacture. In addition, the stick makes it possible to use a very wide range of film laminates made of polymer and/or metal material, that are used as a function of the substances contained in said stick.

This is why the present invention seeks to mitigate the drawbacks of the prior art by proposing a device that is particularly adapted to packaging and administering small volumes of active principles in hydro-alcoholic solution.

In addition, another problem occurs when the total solution to be administered includes at least two elements having instability that requires them to be mixed together only at the moment of administration, the total composition not being stable over time.

To this end, the invention provides a packaging and administering device for administering a hydro-alcoholic solution, the device comprising a deformable container, and a base having a long cannula that is secured to one end of said container so as to deposit said hydro-alcoholic solution very accurately on coming into contact with an oral mucosal zone.

In a particularly attractive first variant that enables gripping and handling to be improved, it is envisaged to add delivery means for delivering the solution contained in said stick, in particular including a pusher and return means.

The device of the present invention is described in detail below in accordance with particular embodiments, given by way of non-limiting example, and with reference to the accompanying drawings in which the various figures show:

FIG. 1: a view of the minimalist embodiment of the packaging and administering device of the present invention.

FIG. 2: a diagrammatic perspective view of a first embodiment of the packaging and administering device of the present invention, prior to being used.

FIG. 3: a diagrammatic perspective view of an embodiment of the FIG. 2 packaging and administering device, after being use.

FIG. 4: a section view of the FIG. 2 packaging and administering device, prior to being used.

FIG. 5: a section view of the FIG. 2 packaging and administering device, in preparation for being used.

Figure 6:
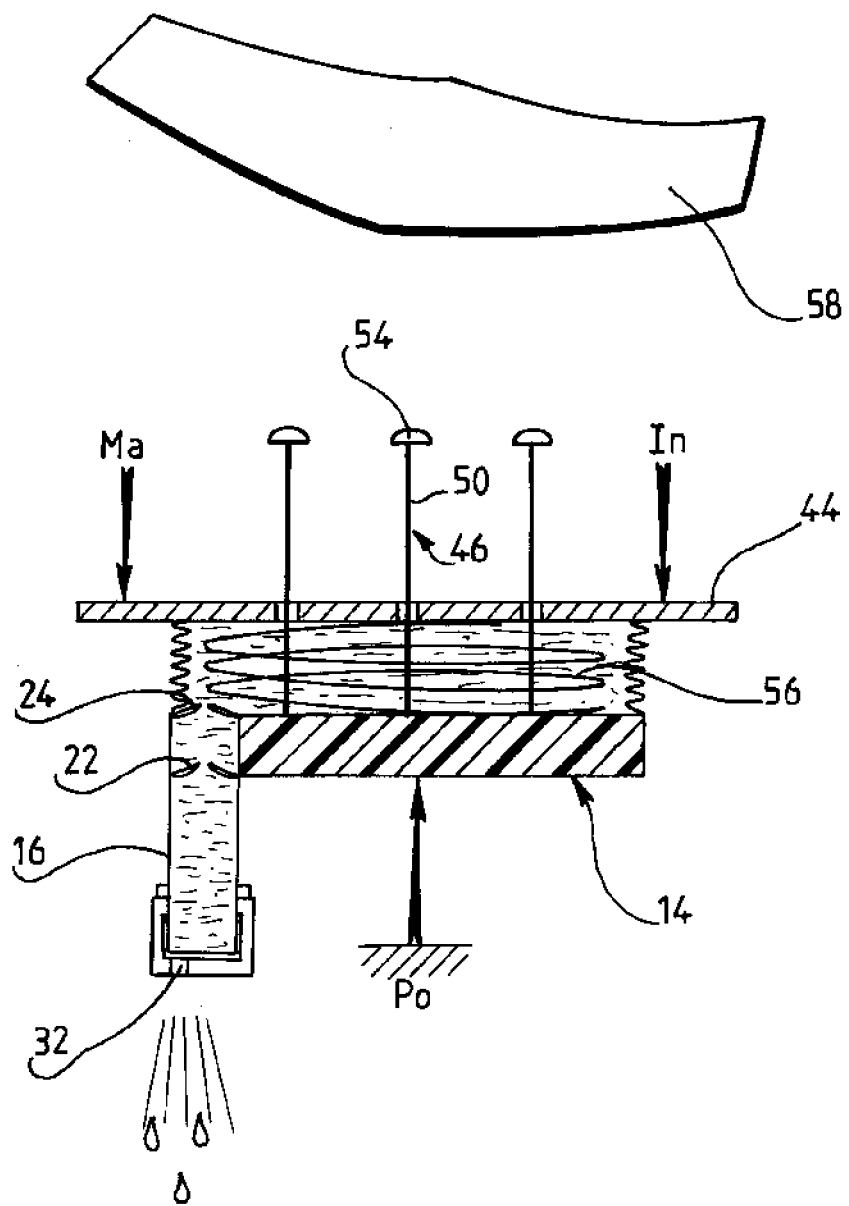

FIG. 6: a section view of the FIG. 2 packaging and administering device, after being use.

Figures 7, 8:
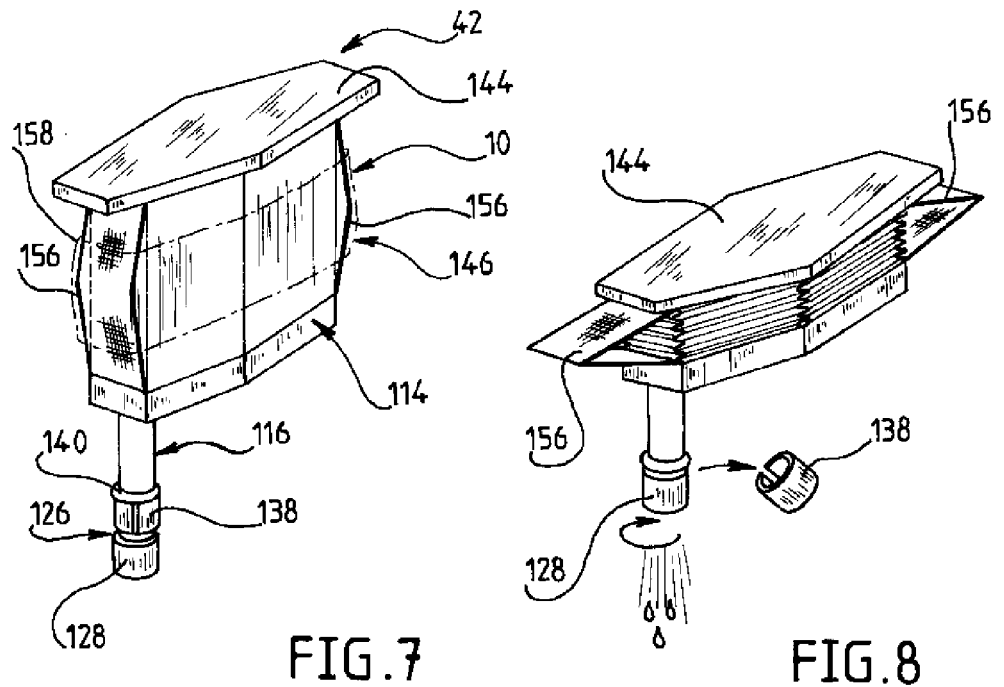

FIG. 7: a diagrammatic perspective view of a second embodiment of the packaging and administering device of the present invention, prior to being used.

FIG. 8: a diagrammatic perspective view of the embodiment of the FIG. 7 packaging and administering device, after being use.

Figures 9, 10:
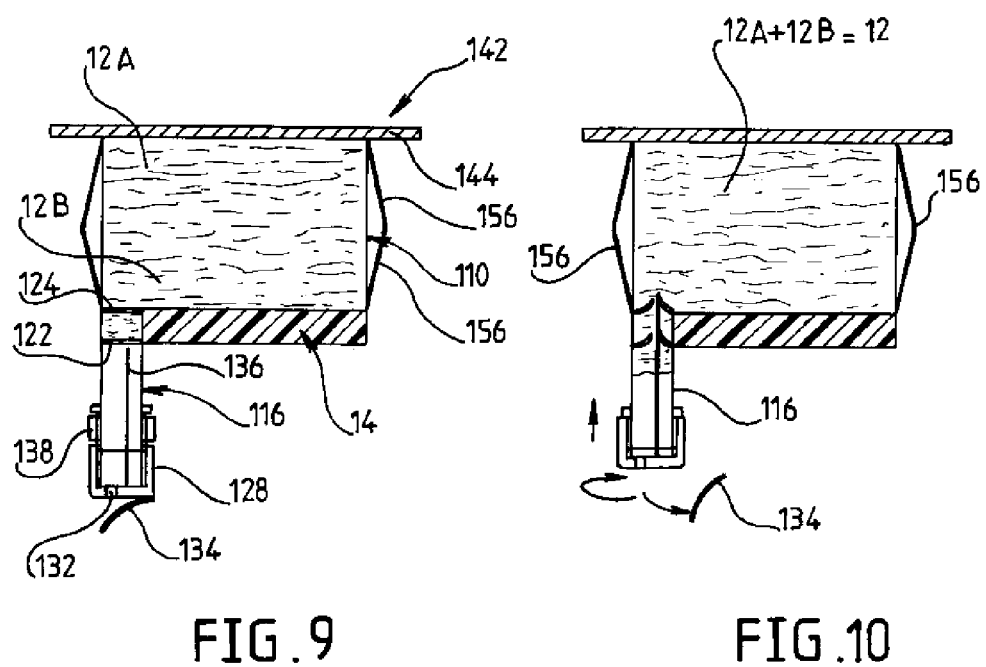

FIG. 9: a section view of the FIG. 7 packaging and administering device, prior to being used.

FIG. 10: a section view of the FIG. 7 packaging and administering device, in preparation for being used.

Figure 11:
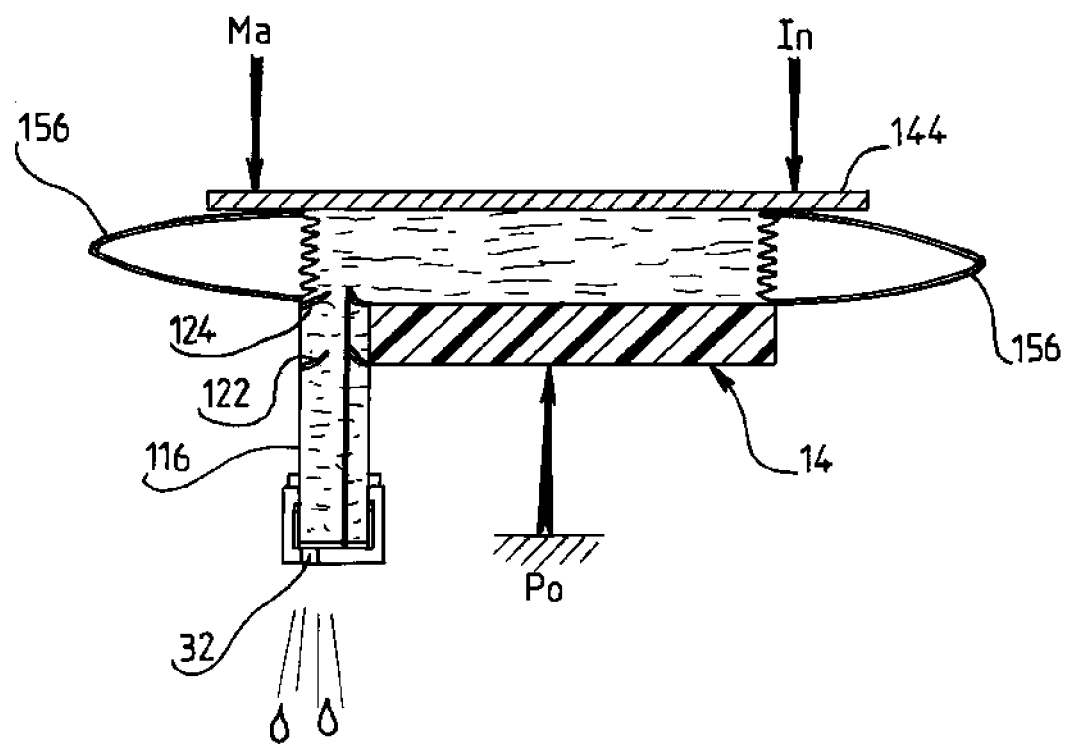

FIG. 11: a section view of the FIG. 7 packaging and administering device, after being use.

The device of the invention is described in its minimalist embodiment in accordance with FIG. 1.

The device of the invention includes a deformable container 10, in particular a pouch that may be made of any deformable material for preserving a solution 12A. Preferably, the container is made of a material that makes it possible to preserve the solution 12A, but also to protect it from the action of light, and to avoid its evaporation through the walls.

The deformable container 10 is secured, in leaktight manner, to a rigid base 14, e.g. made of rigid plastics material.

The device further includes a tube 16 for administering the solution 12. The tube 16 is advantageously secured to the rigid base 14. More specifically, the tube is molded integrally with said base 14.

The tube 16 opens out via its internal end 18 into the container 10. In its inside volume, the tube includes a chamber 20 that is defined by two perforatable membranes 22 and 24 and that is for receiving a second solution 12B for combining with the first solution 12A so as to form the therapeutic solution 12 to be administered.

At its external end 26, the tube 16 carries a cap 28, specifically a screw-fastener cap.

The face 30 may be provided with a delivery hole 32 that is closed by a sealing and safety film 34 that is for pulling off.

The inside of the face 30 also carries a projecting element that forms a needle 36 that points inwards.

Thus, with two solutions to be administered, either the cap 28 is left in place and the film 34 is removed so as to enable administering through the delivery hole 32, or the cap 28 and its needle 36 are removed so as to enable administering via the tube 16.

A removable safety ring 38 is positioned between said cap and an abutment 40 that is secured to said tube 16.

The cap 28 may thus take up two positions, one prior to use, in which everything is sealed and closed, and the other in preparation for use, in which firstly the safety ring 38 is removed, then the cap 28 is screw-tightened until it comes into abutment against the abutment 40, the needle 36 thus perforating the two perforatable membranes 22 and 24, and releasing the solution 12B contained in the chamber 20.

As a result, the two solutions 12A and 12B can mix together, and the therapeutic hydro-alcoholic solution 12 is ready for use and to be administered.

The operation of the packaging and administering device of the present invention, in its minimalist version, is described in detail below with reference to FIG. 1.

The user removes the safety ring 38 and screw-tightens the cap 28 fully so that the needle 36 comes to perforate the membranes 22 and 24.

The composition 12B released from the chamber 20 mixes with the composition 12A of the container 10.

The user either removes the film 34 and releases the hole 32 so as to as to enable the therapeutic composition to be delivered into the oral cavity through the tube 16, or the user removes the cap 28 and its needle.

The user places the end of the tube 16, via is external end 26, under the tongue or in any anatomic zone of the oral cavity.

The user may then squeeze the deformable container and/or may suck so as to ensure that all of the therapeutic composition 12 is delivered completely.

The more air there is in the top zone, the more easily this is performed, said air pressure providing an expulsion effect for expelling the composition.

This embodiment makes it possible to satisfy the various constraints that are imposed.

The problem of unstable compositions of substances is solved since said substances are mixed only at the moment of use, without risk of being mixed beforehand and left on standby. As soon as the container is ready for use, it can no longer be put down or left on standby, it must be administered.

This arrangement also satisfies the constraints imposed by the industry both from the point of view of large-scale production and from the point of view of cost. The container also makes it possible to guarantee the very particular pharmaceutical quality of hydro-alcoholic solutions, acting as vectors for active principles to be administered by oral permucosal path.

In an embodiment described with reference to FIGS. 2 to 5 taken together, the device of the invention further includes delivery means 42 for delivering the solution 12 to be administered.

The delivery means 42 comprise a movable plate 44, guide means 46, and resilient return means 48.

The movable plate 44 is secured to the deformable container 10, facing the base 14. The plate 44 is capable of taking up at least two extreme positions, one in which the plate 44 is at a distance from the base 14, prior to use, the deformable container 10 being full of solution 12A and possibly also of air, and the other in which the plate 44 is pressed against said base, after use, the solution 12 being expelled.

In the embodiment shown, the guide means 46 comprise at least two rods 50, specifically four rods. The rods 50 pass through holes 52 formed in the movable plate 44 so as to enable said plate to be guided while being moved in translation, so as to pass from the first extreme position to the other extreme position. The ends of the guide rods 50 carry heads 54 that avoid the plate being removed from the guide rods.

In this embodiment, the resilient return means 48 comprise a spring 56 of the helical type, advantageously made of plastics material. The diameter of the filament constituting the spring is very small and said spring preferably has a conical winding so as to be able to flatten so as to leave, once compressed, only the diameter of the filament, as lost thickness.

The above-described arrangement is associated with a safety label 58 for disposing on the movable plate 44 so as to enable said plate to be locked, avoiding any accidental movement. The plate is prevented from moving as a result of the heads 54 not being able to project through the plate 44. Advantageously, the label is adhesive.

When the safety label 58 is removed, the plate is released and may be moved in translation.

In this arrangement, it should be observed that the movable plate 44 overhangs so as to enable a grip between a thumb and two fingers. The thumb Po is for bearing against the base 14, held by the tube 16, while the index finger In and the middle finger Ma are placed in natural positions on each end of the plate. These positions are referenced In and Ma in FIGS. 2 and 5.

In a particular embodiment of the invention, in order to give an order of magnitude, for a volume of composition to be administered lying in the range 0.5 milliliters (mL) to 2 mL, the device presents a height lying in the range 3.0 centimeters (cm) to 8.0 cm, a width lying in the range 1.5 cm to 5 cm, and the base 14 presents a height lying in the range 2.0 cm to 5.0 cm, and a width lying in the range 1.0 cm to 3 cm.

In the improved embodiment in FIGS. 2 to 6, the device operates as follows.

The pouch 10 contains the first solution 12A, and the spring 56 of the resilient return means ensures that the pouch is held in its extended shape.

The safety label 58 provides a safety guarantee, and prevents any movement of the movable plate 44 relative to the rods 50 of the guide means 46. The solution is thus preserved without its content being spoilt, and without any risk of accidental breach.

The second solution 12B is contained and preserved in the chamber 20 defined by the membranes 22 and 24 in the tube 16.

The implementation of the packaging and administering device of the present invention consists of the following series of steps.

The user removes the safety ring 38 and screw-tightens the cap 28.

The screw-tightening causes the two membranes 22 and 24 to perforate as a result of the movement of the needle 36, thereby releasing the second solution 12B that may be the active principle. The second solution 12B thus mixes with the first solution 12A present in the deformable container 10, which first solution may be the excipient.

It should be observed that there is no risk of leakage, even when the device is held with the tube 16 facing downwards, firstly since the resilient return means 48 and capillarity forces cause the solution to be retained in the deformable container 10, and secondly since the cap and/or the film 34 provide(s) sealing. When the user wishes to administer the therapeutic solution 12 obtained by mixing together the solutions 12A and 12B, e.g. under the tongue, via the cheeks, or via the gums, the user removes the safety label 58 and takes up a thumb and two-finger grip, with the thumb Po bearing against the base 14, and on the opposite side, the index finger In and the middle finger Ma bearing against the movable plate 44.

The tube is placed via its external end 26 under the tongue, or in the relevant anatomical zones of the oral cavity.

The movement of the movable plate 44 relative to the base 14, against the return force of the resilient return means, which movement remains extremely limited compared to the strength of the fingers, expels the therapeutic solution 12, and propels it out from the device, through the hole 32.

The top zone full of air facilitates this expulsion by an effect of flushing out the liquid volume.

During this operation, the deformable container 10 deforms proportionally.

Finally, at the end of administration, the user may possibly exert a small amount of suction, lips closed around the tube, so as to finish off extracting any residual solution in the deformable container.

It should be observed that the guide means enable the movable plate 44 to move in rectilinear translation.

FIGS. 7 to 11 show a variant embodiment, the major modification being the arrangement of the resilient return means.

In order to facilitate reading, elements that are identical or that provide the same functions have the same references as those in FIGS. 2 to 6, but increased by 100.

In this embodiment, the guide means 146 and the resilient return means 148 that ought to be referenced, are combined together and are given only the reference 146.

The helical-type spring 56 is replaced by flexible blades 156 with fold starters. By way of example, the fold starters are small outward bends. Thus, the width of the blades is much greater than their thickness.

In the present embodiment, two blades 156 are provided for ensuring stable movement.

The guide means 48 of the first embodiment are eliminated in favor of the guide means 148 constituted by the blades 156 themselves. The blades are wide enough to guide the movable plate 144 in translation relative to the base 114.

In this embodiment, a safety label 158 should also be provided. In this instance, it is disposed around the blades, in a mid-plane, like a collar, so as to prevent any accidental bending of the blades.

In this embodiment, the user proceeds in the same way, by turning the cap 128 in order to perforate the membranes 122 and 124 and mix together the solutions 12A and 12B so as to obtain the final therapeutic solution 12.

The user then removes the safety label 158.

The device is ready for use.

It suffices to remove the film 134, if any, so as to release the hole 132 or remove the cap 128 and its needle 136, and position the tube 116 in the mouth under the tongue, against the cheeks, or against the gums, to position the thumb and two fingers, and to exert pressure on the movable plate 144, against the resilient return force of the blades 156. The force remains small compared to the strength available with the fingers and thumb.

The blades 156 bend, and the deformable container 110 folds proportionately expelling a flow of the solution 12 and propelling it out from the device through the hole 132 or through the end of the tube 116.

Finally, the user may possibly exert a small amount of suction, with the lips closed around the tube, so as to extract any residual solution from the deformable container.

It should be observed that the blades 156 ensure that the movable plate 144 moves in rectilinear translation so as to come into register with the base 114.

It should be observed that the proposed lozenge-type section of the deformable container 10, 110 may equally well be an oval or circular section without changing the present invention.

The tube 16, 116 carries a screw cap 28, 128, but a push cap could be a full technical equivalent falling within the ambit of the present invention.

The above description relates to a given arrangement in which there are only two membranes and two solutions, but naturally it is possible to increase this number while remaining within the ambit of the present invention.

In addition, for good understanding, the solutions are described as liquids, but the same would apply if one of the compounds were in powder, paste, gel, or granule form.

However, the final therapeutic hydro-alcoholic composition is itself always a liquid.

In the same way, a chamber is defined within the tube by means of two membranes, but the tube itself may constitute the chamber, and then only one membrane is necessary.

It is also possible to envisage variants that are considered as technical equivalents. Thus, instead of providing movement in translation for a plate against a base, it is possible to provide a pinching movement, the base and the plate being connected at a hinge point and housing the deformable container in the angle formed by the base and the plate, so as to enable said container to be flattened by pinching closed the angle of the pincher.

The invention claimed is:

1. A packaging and administering device for administering a hydro-alcoholic solution by passing through a mucous membrane, the device comprising:
    a container that is collapsible and comprising a first fraction of the solution;
    a base secured to the container;
    an administering tube secured to the base and containing a second fraction of the solution, the administering tube comprising a cap and a chamber in which the second fraction of the solution is contained, the chamber bounded by two membranes, the cap is movable from a first cap position to a second cap position and comprises a needle configured to pierce the two membranes when the cap is moved to the second cap position;
    a movable plate secured to one end of the container and movable from a first plate position to a second plate position to expel the solution, in the first plate position the container is in an uncollapsed state, in the second plate position the container is in a collapsed state with the plate at or close to the base;
    a delivery hole for delivering the hydro-alcoholic solution, the cap closing the delivery hole in a leak tight manner until delivery of the solution.

2. The device of claim 1, further comprising a resilient element for biasing the container to the uncollapsed state.

3. The packaging and administering device for administering a hydro-alcoholic solution by passing through a mucous membrane according to claim 1, comprising a guide that comprises at least one rod secured to the base, the at least one rod mounted to slide through the movable plate and provided with a stopper head.

4. The packaging and administering device for administering a hydro-alcoholic solution by passing through a mucous membrane according to claim 3, comprising a helical return spring disposed in the deformable container.

5. The packaging and administering device for administering a hydro-alcoholic solution by passing through a mucous membrane according to claim 3, comprising a safety label.

6. The packaging and administering device for administering a hydro-alcoholic solution by passing through a mucous membrane according to claim 1, comprising at least two blades that guide the movable plate and that bias the movable plate relative to the base.

7. The packaging and administering device for administering a hydro-alcoholic solution by passing through a mucous membrane according to claim 6, wherein each of the at least two blades includes a fold starter in the form of an outward bend.

8. The packaging and administering device for administering a hydro-alcoholic solution by passing through a mucous membrane according to claim 1, wherein the cap includes said delivery hole for delivering the solution and a film.

9. The packaging and administering device for administering a hydro-alcoholic solution by passing through a mucous membrane according to claim 1, having a volume lying in the range 0.5 mL to 2 mL, a height lying in the range 3.0 cm to 8.0 cm, a width lying in the range 1.5 cm to 5.0 cm, and wherein the base presents has a height lying in the range 2.0 cm to 4.0 cm, and a width lying in the range 1.0 cm to 5.0 cm, for administration under the tongue, via the cheeks, or via the gums.

\* \* \* \* \*